United States Patent [19]
Weller et al.

[11] Patent Number: 5,979,448
[45] Date of Patent: Nov. 9, 1999

[54] CONDOM RETENTION DEVICE WITH A RETAINING STRAP

[75] Inventors: James M. Weller, Blaine; John C. Field, St. Paul, both of Minn.

[73] Assignee: Gain, Incorporated, St. Paul, Minn.

[21] Appl. No.: 08/921,933

[22] Filed: Aug. 27, 1997

Related U.S. Application Data

[63] Continuation-in-part of application No. 08/831,605, Apr. 10, 1997, abandoned, which is a continuation-in-part of application No. 08/638,730, Apr. 29, 1996, Pat. No. 5,667,471.

[51] Int. Cl.⁶ .................................................. A61F 6/04
[52] U.S. Cl. ........................................... 128/844; 128/918
[58] Field of Search ..................... 128/842, 844, 128/918; 604/347–353

[56] References Cited

U.S. PATENT DOCUMENTS

| | | | |
|---|---|---|---|
| 5,158,556 | 10/1992 | Starley | 128/844 |
| 5,327,911 | 7/1994 | Pien | 128/844 |
| 5,360,390 | 11/1994 | Maanum | 600/39 |
| 5,531,230 | 7/1996 | Bell | 128/842 |

*Primary Examiner*—Michael A. Brown
*Attorney, Agent, or Firm*—Merchant & Gould P.C.

[57] ABSTRACT

A device is provided for use to retain a condom or similar construction on the penis of a wearer, during intercourse. The device includes a trough member and an arrangement for maintaining the trough member in operative association on the user's penis, during performance of intercourse. A combination including a condom and such a device is also provided, as well as a method of use.

12 Claims, 9 Drawing Sheets

CONDOM RETENTION DEVICE WITH A RETAINING STRAP

CROSS-REFERENCE TO RELATED APPLICATIONS

The present application is a continuation-in-part of co-pending application Ser. No. 08/831,605 filed Apr. 10, 1997, now abandoned, which is a continuation-in-part of application Ser. No. 08/638,730, filed Apr. 29, 1996, now U.S. Pat. No. 5,667,471. The complete disclosures of the above two applications are incorporated herein by reference.

FIELD OF THE INVENTION

The present invention generally relates to devices to assist sexual activity. The invention more specifically concerns devices utilizable to maintain a condom or similar device in place on a human penis, during sexual activity.

GENERAL BACKGROUND OF THE PRESENT INVENTION

A condom is used on the human male for a variety of reasons. The typical reasons are to prevent transmission of disease and/or to prevent pregnancy. In use, the condom can sometimes slip off the human male. This is especially prevalent if the human male's penis becomes flaccid or only partially engorged. If the condom slips off the penis, its effectiveness can be compromised.

SUMMARY OF THE PARENT DISCLOSURE SER. NO. 08/831,605

According to U.S. Ser. No. 08/831,605 there is provided a prosthesis for use by a human male in supporting the penis during sexual intercourse. The preferred prosthesis comprises an elongate trough member of unitary, molded, construction, without any seams, sized to fit over the penis of a user at a location immediately in front of the pubic bone, with the trough member having a longitudinal slot extending completely therethrough, and the trough member having first and second rounded ends. The longitudinal slot is oriented under the penis, in preferred use. The prosthesis has a retaining construction secured to the trough member second end for maintaining the trough member in operative association over the user's penis, during the performance of sexual intercourse, with the retaining construction preferably comprising a retaining tab, and a retaining strap having structure thereon for selective locking engagement with the retaining tab. Preferably both the retaining tab and retaining strap are thinner than the second end of the trough member. Also, preferably both the retaining strap and the retaining tab are secured to the trough member second end so that an outer shoulder is formed along the trough member second end, between each of the retaining strap and retaining tab, and an outer surface of the trough member.

When a condom or similar device is placed over the trough member, the outer shoulder aids in maintaining the condom or similar device in place on a human penis, during sexual activity, in addition to the other advantages of the parent application.

In a preferred embodiment the retaining tab has a first end whereat it is molded to the trough member; and, (1) a first end of the retaining tab has a first dimension of width; and, (2) the tab is configured to have a second dimension of width, at a portion thereof spaced from said trough member, which is greater than the first dimension. In certain preferred embodiments, the second dimension of the tab is at least 0.75 times larger than the first dimension. Typically, the tab second dimension will be 1 to 4 times larger than the first dimension. In some preferred applications, the first dimension of width will be within the range of about 0.25 to 0.5 inches and the second dimension of width will be in the range of about 0.5 to 1.0 inches.

In a typical embodiment, the prosthesis has a trough member with an overall length in projection of 2 to 4 inches. In typical applications, the trough member first end also has an inside edge having a radius of curvature that is less than 0.03 inches; and, the trough member first end has an outside edge having a radius of curvature between 0.02 and 0.03 inches. Also, typically the trough member second end has an inside edge having a radius of curvature that is less than 0.03 inches; and, the trough member second end has an outside edge having a radius of curvature between 0.05–0.1 inches.

In typical applications, the prosthesis has a trough member first end with a thickness of about 0.02–0.08 inches; and, a trough member second end with a thickness of about 0.2–0.3 inches. In certain preferred embodiments, the prosthesis has a trough member first end molded to a radius of curvature of about 0.55–0.58 inches; and, a trough member second end molded to a radius of curvature of about 0.6–0.75 inches. For some preferred embodiments the thickness of the trough member decreases laterally from the center to the edges or corners.

The drawings constitute a portion of the specification and include exemplary embodiments of the present invention. It will be understood that in some instances relative component sizes and material thicknesses may be shown exaggerated, to facilitate an understanding of the invention.

SUMMARY OF THE INVENTION

According to one aspect to the present invention there is provided a condom retention device for use by a human male in retaining a condom over the penis during sexual intercourse. The preferred condom retention device comprises a member of unitary, molded, construction, without any seams, sized to fit over the penis of a user at a location immediately in front of the pubic bone. In some preferred embodiments the member has a longitudinal slot extending completely therethrough, and the member has first and second rounded ends. The longitudinal slot is positioned under the penis, in some preferred uses. The condom retention device has a retaining construction secured to the member second end for maintaining the member in operative association over the user's penis, during the performance of sexual intercourse. In some preferred embodiments the condom retention device is designed similarly to the retaining constructions described in Parent application Ser. No. 08/831,605.

For some preferred embodiments the thickness of the member decreases laterally from the center to the edges or corners.

The drawings constitute a portion of the specification and include exemplary embodiments of the present invention. It will be understood that in some instances relative component sizes and material thicknesses may be shown exaggerated, to facilitate an understanding of the invention.

BRIEF DESCRIPTION OF THE DRAWINGS

FIG. 2 is an end elevational view of the arrangement shown in FIG. 1; FIG. 2 being from the viewpoint of line 2—2, FIG. 1.

FIG. 6 is a top plan view of the arrangement shown in FIG. 1; FIG. 6 depicting, in phantom, an optional condom or lubricated cover which may be utilized in association with the arrangement.

FIG. 9 is a fragmentary end view of another embodiment of a device in the U.S. parent application Ser. No. 08/831,605; FIG. 9 being from a similar view point to FIG. 3.

FIG. 11 is an end elevational view of the arrangement shown in FIG. 10; FIG. 11 being from the viewpoint of line 11—11, FIG. 10.

FIG. 17 is a fragmentary end of view of another embodiment of the present invention; FIG. 17 being from a similar viewpoint to FIG. 12.

DETAILED DESCRIPTION

Herein a detailed description of the present invention is provided. The description is made with reference to accompanying drawings, and specific features of the preferred embodiments depicted therein. It is to be understood that the specific features of the drawings are intended to be exemplary, for a general understanding of the basic principles of the present invention.

The present invention is, in part and in some embodiments, an improvement in the arrangements described in U.S. Pat. No. 5,360,390 issued Nov. 1, 1994, and presently owned by Gain, Inc. of Minneapolis, Minn., the assignee of the present invention. Before specific improvements relating to the present invention are described, a specific description of some of the prior art arrangements of U.S. Pat. No. 5,360,390 will be presented. A discussion of the arrangements of the parent application Ser. No. 08/831,605 will also be presented. The complete disclosure of U.S. Pat. No. 5,360,390 and Patent application Ser. No. 08/831,605 are incorporated herein by reference.

I. U.S. Pat. No. 5,360,390

In one embodiment of the prosthesis in U.S. Pat. No. 5,360,390, a device is disclosed which comprised a trough-shaped member having a generally C-shaped cross-section. According to 5,360,390 an embodiment of the device was a molded construction comprising flexible urethane or latex which had selected varying thicknesses throughout to achieve advantage. That embodiment was preferably formed from a flexible high memory material which was somewhat elastic. Thus, it could be stretched open radially, fit over the penis of a wearer and then allowed to collapse and snugly fit around the penis of a wearer. According to 5,360,390 a preferred, comfortable, snug fit could be obtained by shaping the article such that the position of memory or rest was at a radial size that would be comfortable for the intended user. According to 5,360,390 an advantage from allowing for radial flexibility was that the device could be expanded more toward one end than another; i.e. it can be expanded more toward the pubic area of the wearer than further along the shaft of the penis.

According to 5,360,390 preferred materials for construction of the trough member of the arrangement were FDA approved thermoplastic rubbers, such as natural (coverless) Monsanto Santoprene®, in U.S.P. class no. 6. This was a pharmaceutical medical material known to be safe when positioned in a body cavity and/or when subjected to body fluids. It could be obtained from Monsanto in a variety of thicknesses, depending upon heat and pressure applied, and could be readily molded into configurations such as those shown in 5,360,390.

In U.S. Pat. No. 5,360,390 it was described that, preferably, this embodiment be constructed with a longitudinal dimension (length) approximately ⅓ to ⅔ (preferably at least ½) of the length of the flaccid or partially engorged penis (i.e. the penis as engorged as the particular individual was able to maintain). For the average male, the length of the partially engorged penis was described as being about 4.0 to 5.0 inches. The preferred average length of the embodiment of the device, for the average male, was described in U.S. Pat. No. 5,360,390 as about 2–3 inches, and preferably about 2.25–2.75 inches.

In U.S. Pat. No. 5,360,390 it was described that in preferred embodiments, the inner surface of the device was provided with pebbling, to increase its coefficient of friction against skin, to help retain the device in place, during use.

The arrangement of one embodiment of the device was mounted with a stirrup or strap. The strap was connected at opposite ends to the trough member. The strap was sized to extend around a portion of the body of a wearer. According to 5,360,390 it could extend, for example, around the scrotum of a wearer.

According to 5,360,390 in one arrangement, the strap was connected at one end by molding or similar means; and, the opposite end of the strap included means thereon for engagement with connector means on the trough member. In one arrangement, connection was facilitated by a low-profile slot arrangement engageable by a ball and link type fastener. According to 5,360,390 the user would extend the strap into the slot of the connector, adjusting the amount of extension into the slot for comfort; and the excess portion of the strap would be torn or cut off and discarded. When the device was to be removed, a remaining link could be premolded to break, preventing reuse.

According to U.S. Pat. No. 5,360,390, an alternate mounting system for the strap was also disclosed. The strap was connected at one end to the trough member. According to 5,360,390 the connection could be made by molding or similar means. At the other end the strap included a "ratchet" or "directional tooth" fastener, receivable within the connector. According to 5,360,390 the user could adjust the length of the strap by the extent to which the strap was threaded through a receiving slot in the connector; and, the excess portion of the connector could be torn or cut off and discarded. The portion of the strap having a tooth fastener thereon could be readily torn, for removal of the device from a user.

II. Detailed Description of Arrangements According to the Invention of the Parent application Ser. No. 08/831,605. FIGS. 1–9

As indicated, the above discussion reflects some of the arrangements described in U.S. Pat. No. 5,360,390 issued Nov. 1, 1994, and assigned to Gain, Inc. The description provided above with respect to these arrangements, reflects the substance of descriptions provided in that patent for some of the embodiments.

Since the time of issuance of U.S. Pat. No. 5,360,390, Gain, Inc., the assignee of the present invention, has developed improvements in the arrangement (prosthesis) while preparing the arrangement for marketing. The improvements in connection with the arrangement described in application Ser. No. 08/831,605 are presented herein and are reflected in the drawings of FIGS. 1–9. It will be understood that the arrangement of FIGS. 1–9 in many ways functions generally analogously to the arrangements described in connection with U.S. Pat. No. 5,360,390, and may be, except as described hereinbelow, constructed from similar materials and of similar dimensions. Certain specific improvements are provided, however, to advantage.

Figure 1:
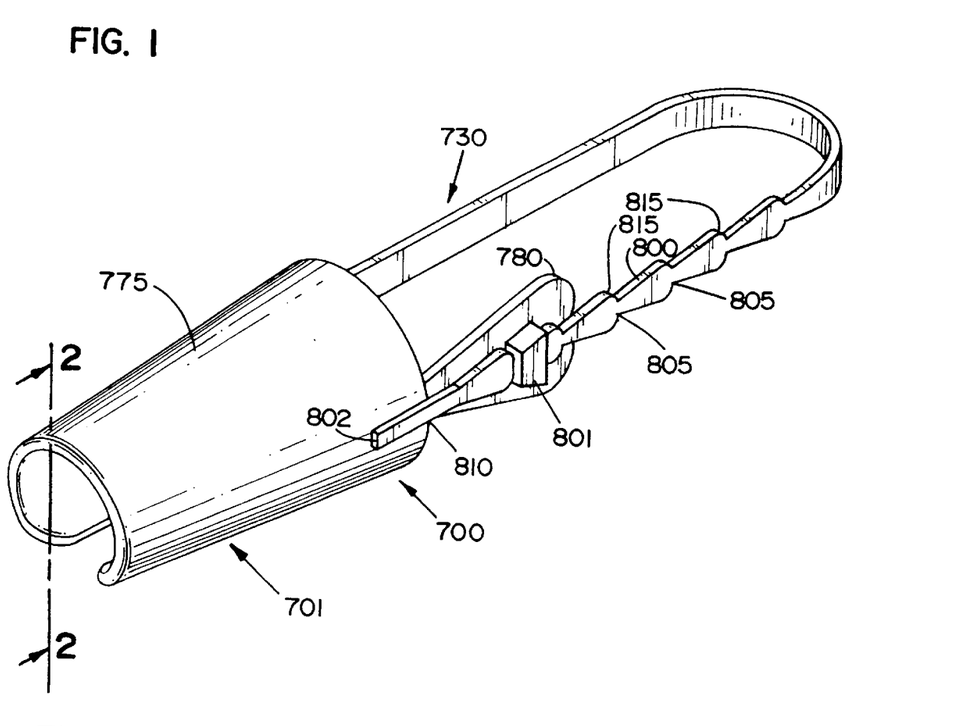
FIG. 1 is a perspective view of a device according to the parent U.S. application Ser. No. 08/831,605.
Figure 2:
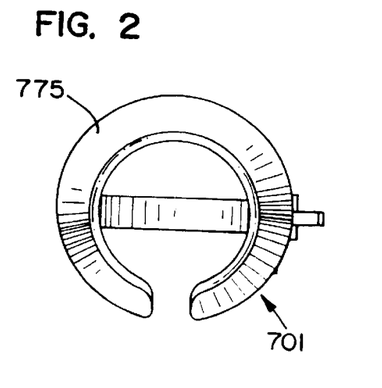

Referring first to FIG. 1, the prosthesis or arrangement is shown generally at reference numeral 700. Preferably, the entire arrangement 700 is a molded construction comprising flexible urethane or latex, most preferably the preferred Monsanto Santoprene® described above. That is, most preferably the arrangement 700 is of unitary construction, completely molded, with no attached parts that are not part of the integrally molded construction; i.e. there are no seams or points of similar attachment.

The arrangement 700 generally includes one elongate trough or trough-shaped member 701; and, a mounting strap 730. The trough member is sized to fit over a penis of a user at a location immediately in front of the pubic bone. The trough member preferably has a C-shaped cross section and longitudinal slot extending completely thereacross, as described and shown the slot is on an underside of the trough 701, similarly to arrangements previously described.

Figure 8:
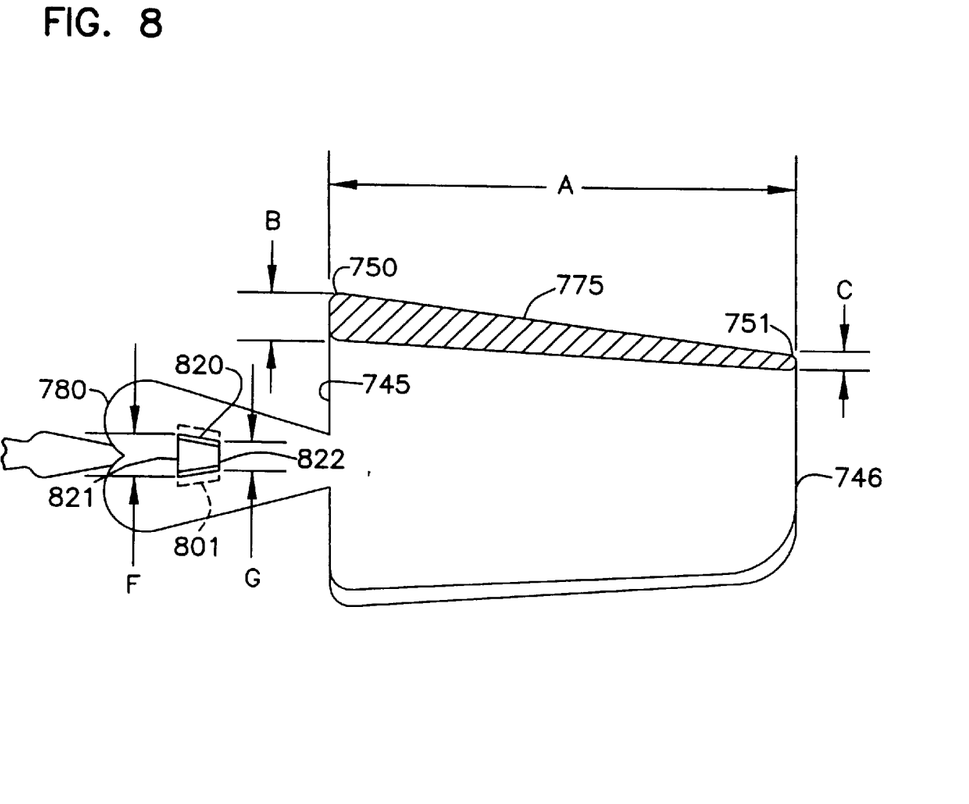
FIG. 8 is a fragmentary cross-sectional view of the arrangement shown in FIG. 1, taken generally along line 8—8, FIG. 6.

In addition to being molded from the Monsanto Santoprene® described above, preferably the trough member 701 of arrangement 700 is as follows: its overall length, preferably as measured in projection as indicated in FIG. 8 at dimension A, is preferably 2–4 inches, more preferably 2.25–2.75 inches, and for the preferred construction is about 2.44 inches. (By "in projection" reference is meant to the length of the projected image, as shown, which may be slightly shorter than the actual length of the surface.) The thickness at dimension B, FIG. 8, is preferably about 0.2–0.3 inches, most preferably about 0.22–0.28 inches, and in the preferred commercial arrangement is about 0.25 inches. The overall analogous thickness at the end represented at C, in FIG. 8, is preferably about 0.02–0.08 inches, most preferably about 0.05 inches. In the preferred arrangements, the trough member is molded from a material that has a durometer reading of less than 70, more preferably a durometer reading of 55 to 65, and most preferably a durometer reading of 64. Preferably, the inside dimension at end 745, FIG. 8, is molded to a radius of curvature of about 0.55–0.9 inches, preferably about 0.62–0.75 inches, most preferably about 0.69 inches. Of course, because the material is preferably a flexible Santoprene®, once removed from the mold it may curl to a smaller radius of curvature, but it will readily flex to the appropriate radius of curvature if of the thickness as described. Preferably, the analogous inside radius of curvature at end 746, FIG. 8, is molded to a radius of curvature of about 0.05–0.2 inches smaller than the inside radius of curvature of end 745, and in typical preferred arrangements it is a radius of curvature of about 0.5–0.63 inches and preferably about 0.55–0.58 inches. Most preferably it is about 0.56 inches when end 745 is about 0.69 inches. In use, the arc made by the preferred embodiment of the trough-shaped member 701 will consist of an arc of between about 200 to 340 degrees, and most preferably between about 240 to 300 degrees.

The radii of curvature at certain portions of the arrangement have been designed for preferred levels of comfort. The radius of curvature at edge 750 (the outer edge of end 745) is preferably molded to a radius of about 0.03–0.1 inches, more preferably at least about 0.05 inches, and for the preferred arrangement about 0.06 inches. The radius of curvature at edge 751 (the outer edge of end 746) is preferably 0.01–0.04 inches, most preferably about 0.02–0.03 inches, and for the most preferred arrangement is about 0.025 inches.

Figure 7:
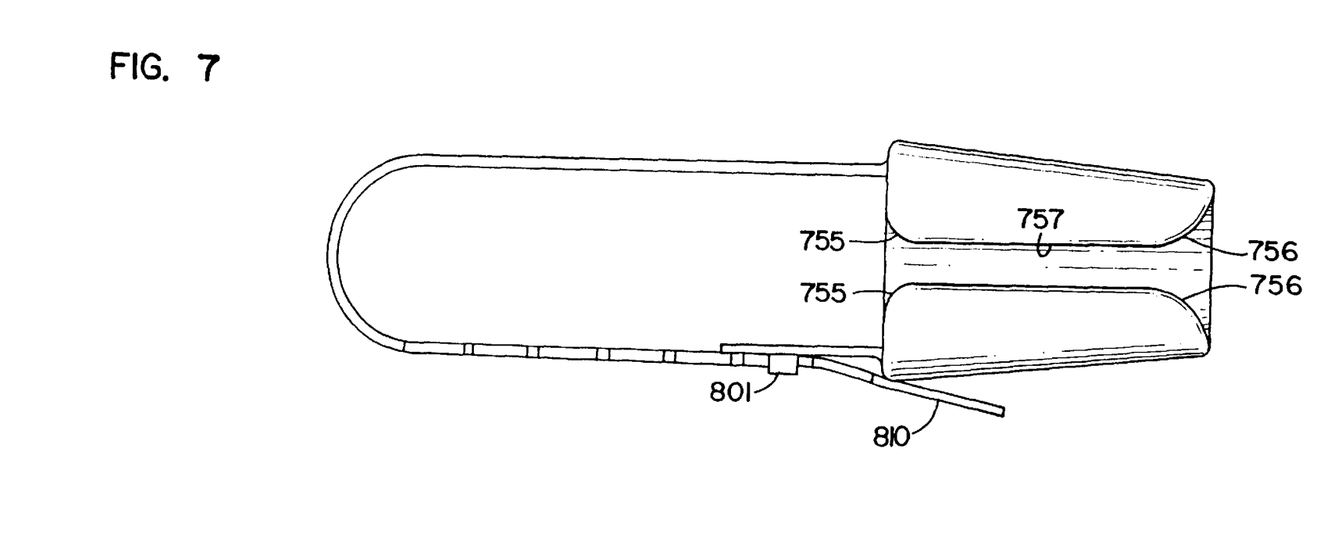
FIG. 7 is a bottom plan view of the arrangement shown in FIG. 1.

Referring to FIG. 7, preferably the radius of curvature for edges or corners 755 is about 0.1–0.3 inches, most preferably about 0.2–0.25 inches, and for the preferred arrangement is 0.22 inches. Slot 757, FIG. 7 may be as described above for U.S. Pat. No. 5,360,390, with a similar width and definition by arcuate extension.

At corners 756, FIG. 7, preferably the radius of curvature is about 0.02–0.08 inches, more preferably 0.03–0.07, and for the most preferred arrangement is about 0.05 inches.

It has been found that when molded to the general dimensions described hereinabove, arrangements 700 according to the present invention will be shaped in a convenient, comfortable, manner that is effective for facilitating use, on the average wearer.

Attention is now directed to features which concern the mounting strap 730, FIG. 1, and the manner in which it is mounted in the arrangement 700. The mounting strap serves as part of a form of retaining structure for maintaining the trough member in operative association over the user's penis, during intercourse. Although alternatives are possible, the preferred retaining structure comprises a retaining strap 730 and an associated tab 780.

Figure 6:
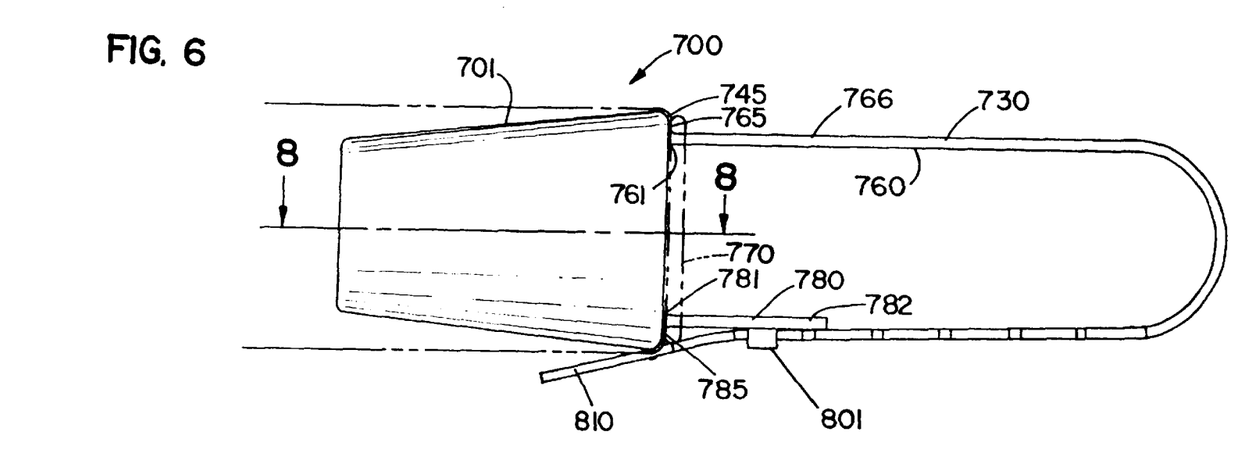

Referring to FIG. 6, strap 730 is part of the overall molded arrangement 700 and, thus, is integral with portion 701, i.e. there is no seam therebetween. Preferably, it is molded such that an inside surface 760 of strap 730 is approximately flush with (or coplanar with) an inside surface of portion 701. By constructing the overall molded arrangement 700 such that an inside surface 760 of strap 730 is approximately flush with (or coplanar with) an inside surface of portion 701, instead of having the inside surface 760 or an outside surface 766 of strap 730 approximately flush with (or coplanar with) end 745 of trough member 701, the strap 730 is much less likely to break away from the end 745 of trough member 701, in use. Also preferably strap 730, at point 761, FIG. 6, whereat it is attached to trough member 701, has a thickness which is no more than about two-thirds of the thickness of end 745 of trough member 701 at this location. Preferably, the thickness of strap 730 is about 0.02–0.1 inches, more preferably about 0.05–0.09 inches, and for the most preferred arrangement described is about 0.07 inches, throughout. In the preferred embodiments, preferably an outer lip or shoulder at 765 where strap 730 attaches to trough member 701 is left. This lip or shoulder 765 provides a recess into which an open end of a condom or lubricated cover, shown in phantom in FIG. 6 at reference numeral 770, can be positioned (rolled) in use. This shoulder 765 will tend to maintain the condom or lubricated cover securely on the user and arrangement 700, during use, to advantage. In some preferred embodiments this is facilitated by the absence of a bead along outer surface 775, of trough member 701, FIG. 1. That is, referring to the cross-section of FIG. 8, in some preferred embodiments outer surface 775 generally is flat or planar, with the curved ends as described, and it does not have an upwardly or outwardly raised bead or projection thereon, at any location, and the outer surface 775 has rounded ends 751 and 750 as described. In other preferred embodiments, outer surface 775 may have a series of raised ribs along its length, or a series of bumps or other surface configurations.

Referring to FIG. 6, preferably the arrangement 700 includes a receiving tab 780 molded to trough shaped member 701 at a location 781 generally opposite of location 761 whereat strap 730 attaches. Preferably, member 780 has a thickness generally the same as that of the strap 730. Also preferably, it is analogously molded with an inside surface 782 approximately flush or coplanar with an inside surface of trough shaped member 701. Further, preferably it is molded such that shoulder 785, analogous to shoulder 765, is provided, for analogous reasons.

Figure 5:
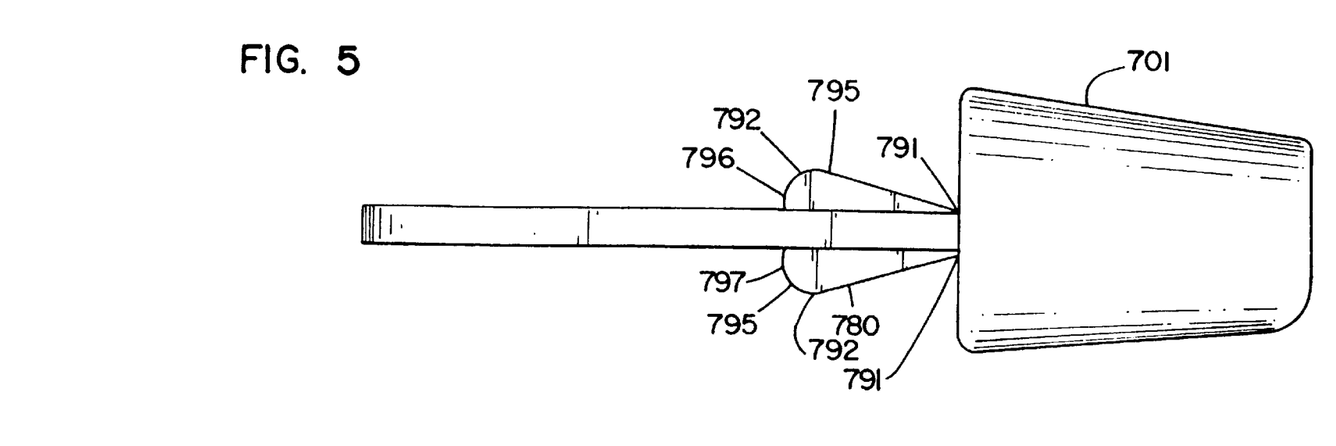
FIG. 5 is an opposite side elevational view to that shown in FIG. 4.

Referring to FIG. 5, preferably member 780 has a relatively narrow dimension at location 791 whereat it is attached to trough shaped member 701, and a relatively wider dimension, somewhere else throughout its extension. For the arrangement shown in FIG. 5, the relatively wide dimension occurs between points 792. This facilitates operation. First, the relatively narrow dimension at region 791 helps provide for such features as: ease of molding and secure positioning of a condom or lubricated cover over the arrangement. The relatively wide dimension between points 792, however, facilitates comfort for the wearer, since it expands the width of tab 780 where it rests against the skin of the user. In preferred arrangements, between points 791, FIG. 5, the arrangement 700 has a dimension of about 0.75 to 1 inches and preferably about 0.87 to 0.94 inches. Also for preferred arrangements, the tab or member 780 has a dimension thereacross, at its widest point, of at least 1.1 times that of the dimension between points 791; with the dimension being typically about 0.12 to 0.88 inches and most preferably at least about 0.37 inches.

Figure 4:
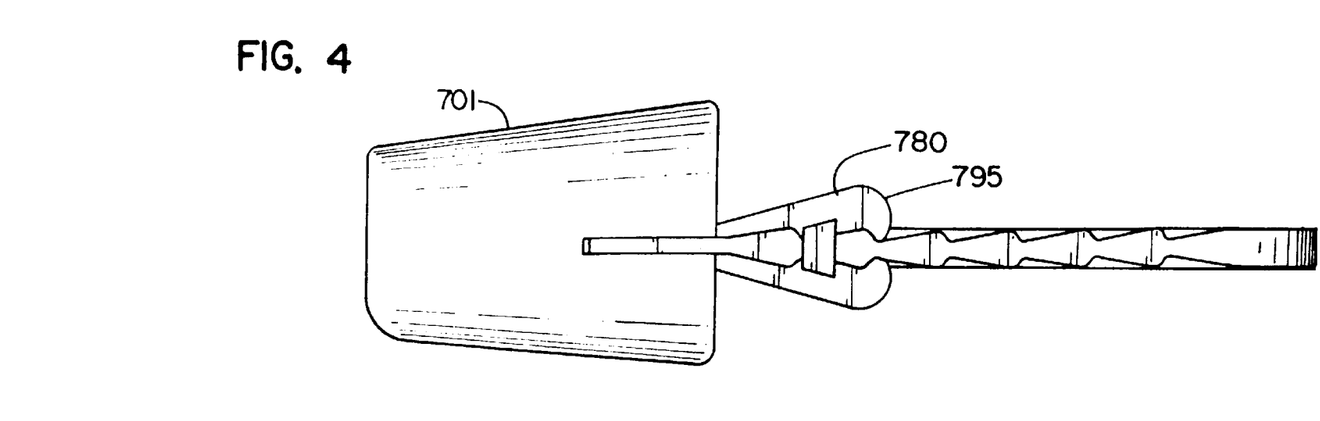
FIG. 4 is a side elevational view of the arrangement shown in FIG. 1.

The particular "heart shaped" outer configuration for member 780 illustrated in FIGS. 4 and 5, by periphery 795, provides no distinct advantage, and is present as an artistic feature for aesthetic purposes. Also, in part, it was designed to serve a distinctive source identifying function, i.e., that the arrangement originated with the present assignee. It will be readily understood that advantageous narrow portions at area 791, and a wide portion somewhere else in member 780 could be accomplished with many variations in outer periphery. The two rounded lobes at 796 and 797, provide a somewhat "heart-shaped" design, and do not specifically serve advantage.

Again, there is, however, advantage to having a relatively wide portion as indicated between points 792. A wide dimension at such a location, in tab 780, provides for comfort for the wearer, and avoids a relatively narrow strap which might tend to dig into the skin of the wearer a bit more at this location. The relatively wide portion as indicated between points 792 also has advantage by reducing the pulling of the user's pubic hairs when strap 730 is being attached to tab 780.

Referring to FIG. 1, strap 730 includes a notched section 800 therein, and tab 780 includes a locking arrangement such as a catch 801 therein, for receiving end 802 of strap 730 therethrough. In preferred arrangements the length of strap 730 from point 761 to the beginning of the notched section 800 is about 3–6 inches in length, and most preferably is about 4.5 inches in length. A variety of designs can be utilized for notches 805 and catch 801. For the arrangements shown, catch 801 is a raised slot through which selected notches 805 extend. In preferred embodiments, the raised slot has a height of about 0.03–0.11 inches, more preferably about 0.06–0.10 inches, and for the most preferred arrangement described is about 0.08 inches. All that is generally required is a secure arrangement, to facilitate attachment of the wearer. For typical preferred arrangements, strap 730 from end to end will be molded to be about 9 to 11 inches long, so that it can be used conveniently by a variety of users, and tab 780 will be about 1 to 1.5 inches long, most preferably about 1.19 inches long. If desired, the user could cut off the extension or tab 810 projecting beyond catch 801, FIGS. 1 and 7, after the device 700 has been positioned on the user, for comfort. It could be retained, however, in many instances. In connection with this, referring to FIG. 6, the tab 810 is shown projecting on the outside of the condom or lubricated cover. It could alternatively be positioned under the condom or lubricated cover, if desired. As a further alternative, tab 810 could be cut to a length that would allow it to rest substantially parallel to tab 780, between a catch arrangement 801, FIG. 1, with the distal end of tab 810 being truncated so as not to extend as far as the condom or lubricated cover.

Devices as shown in FIGS. 1 through 8 could be manufactured for single use, or for multiple use. When multiple use is desired, it will be preferred to have a catch arrangement 801, FIG. 1, which, although secure, does allow for retraction of tab 810 for disconnection. Rounded edges 815, on notches 805, FIG. 1, facilitate this. In the preferred embodiments, the rounded edges 815 are about 0.12–0.4 inches in width, and most preferably about 0.25 inches in width. In preferred embodiments, the notches 805 and tab 810 are 0.07–0.20 inches in width, and most preferably about 0.12–0.13 inches in width. To facilitate insertion and removal of tab 810 with catch arrangement 801, it is preferable to have the rounded edges 815 have a radius of curvature in the range of 0.03–0.09 inches, most preferably 0.06 inches. In the preferred embodiments, it is preferable to have the notches 805 also somewhat rounded, preferably in a range of 0.005–0.02 inches, most preferably 0.01 inches. In order to accommodate a variety of individual sizes, it is preferable to have a plurality of pairs of rounded edges 15 provided on Section 800 of strap 730, more preferably, a series of 4–14 such pairs of rounded edges 815 are provided, and most preferably eight pairs of rounded edges 815 are provided. The distance between a first pair of rounded edges 815 and a second adjacent pair of rounded edges 815 is preferably in the range of about 0.25–1 inches, and most preferably about 0.5 inches. The length of tab 810 is preferably in the range of about 0.5–2 inches, and most preferably about 1 inch.

Figure 9:
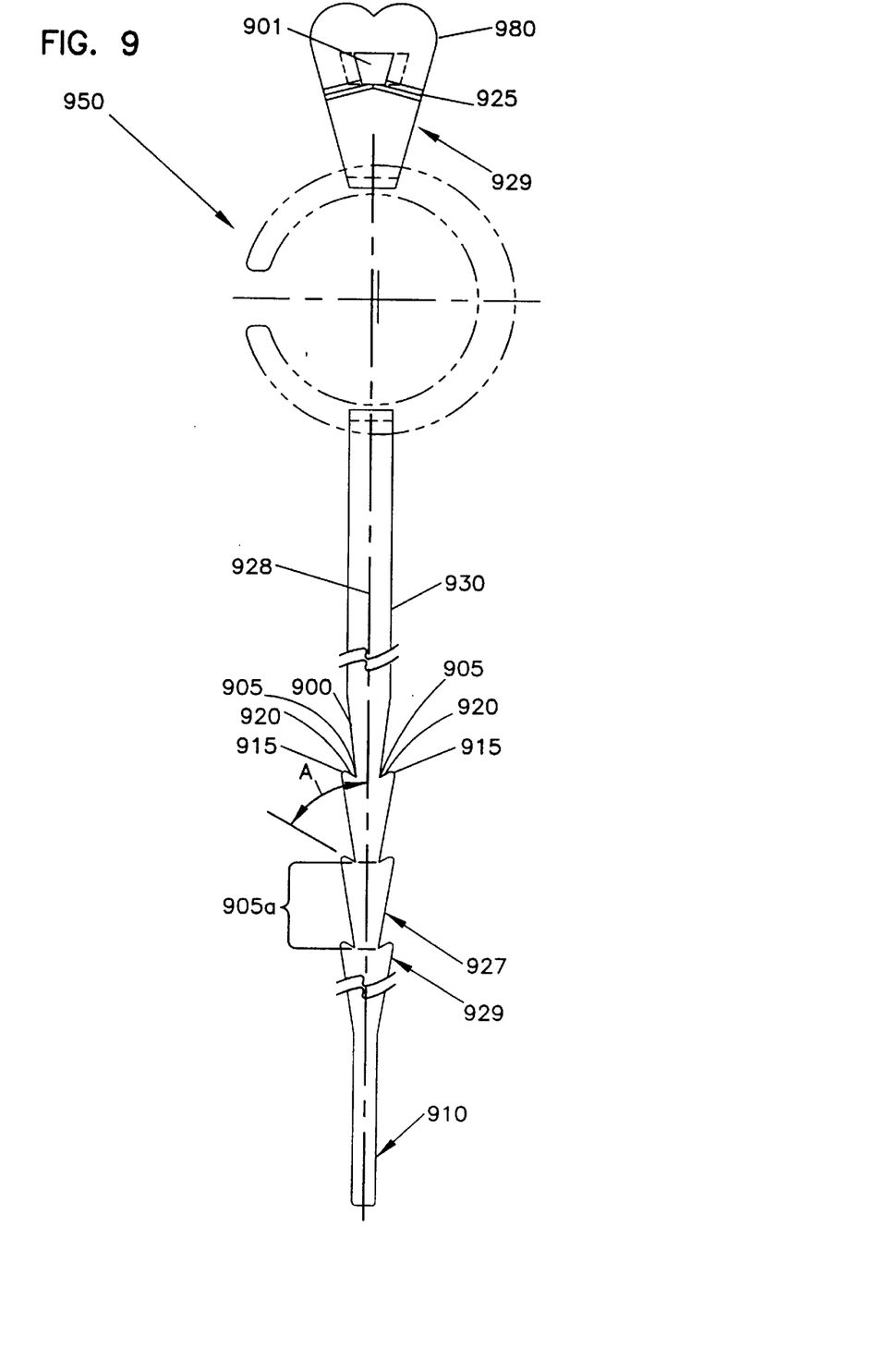

When single use is desired, it may be preferred to have a device 700 which does not allow for easy retraction of strap 730, FIGS. 1 and 6, without breaking the device 700. In FIG. 9, an example of a modified device 950, that is generally analogous in detail to the device 700 described in FIGS. 1–8, except as described hereinbelow, is depicted. In the preferred embodiment depicted in FIG. 9, the notched section 900 of strap 930 includes a plurality of engagement segments 927, with each engagement segment extending from rounded edge 915 toward a tab 910, and ending at the next succeeding notch 905.

In the preferred embodiment for single use depicted in FIG. 9, notch 905 is deepened, compared to notch 805, FIG. 1, by providing a sloped shoulder 920, on rounded edge 915. In the preferred embodiment shown in FIG. 9, the narrowest region, between opposing notches 905, is about 0.06–0.18 inches in width, and most preferably about 0.11–0.13 inches in width. In preferred embodiments, as depicted in FIG. 9, sloped shoulder 920 will form an acute angle A with a line 928 generally parallel to strap 930. Sloped shoulder 920 provides substantial tension when tab 910 is retracted from catch 901. Thus, sloped shoulder 920 forms a one-way ratchet/catch system 929 which cannot readily be reversed, but rather which must be broken to be easily disengaged. In addition, notches 905 are configured to provide a narrowing in region 905a along the notched section 900 of strap 930, which allows for relatively easy breakage of strap 930, upon attempted retraction of tab 910, by comparison to strap 730 (FIG. 1). Thus, after one use, the device 950 will likely have been broken by the user. This helps ensure that the device 950 will only be used once.

Also preferably one-use arrangements such as shown in FIG. 9 include tear points or weakening points therein to help ensure that after one use, when the device is removed, the device will break so that it will not be reused. Tear lines or weakening lines can be provided by using score lines, grooves, perforations, or other arrangements in selected portions of the assembly that will be under tension, when an effort is made to remove strap 930 from catch 901. For example, in FIG. 9, tab 980 is shown including a weakening groove 925. Score line(s) or groove(s) similar to groove 925 would facilitate breakage of tab 980, upon application of forces to retract tab 910 from catch 901. Although groove 925 is illustrated as having a V-shape, it will be appreciated that other shapes will work. Grooves which extend about 30% to 80%, typically about 50%–70%, through the thickness of the tab 980 or strap 930 will generally be preferred.

Of course, groove 925 can alternatively comprise opposing grooves on both sides of tab 980. Alternatively, weakening in tab 980 to facilitate breakage upon attempts to disengage strap 930, could be provided by perforations rather than grooves. It is noted that weakening in tab 930, by grooves, score lines, perforations, etc. may also be used to facilitate breakage.

Referring to FIG. 8, catch 801 has an opening 820 to receive strap 730, such that the strap 730 may be lockingly retained by any of the pairs of rounded edges 815 on Section 800 of strap 730. In order to facilitate insertion of end 802 of tab 810 into opening 820 of catch 801, it is more preferable that opening 801 have a first end 821 with a width F that is wider than the width of tab 810. Also in the preferred embodiments, it is advantageous to have the opening 820 have a second end 822 with a width G that is smaller than width F of end 821, but larger than tab 810, more preferably, width G is in the range of about 0.01–0.25 inches in width, and most preferably 0.15 inches in width.

Referring to FIG. 8, in preferred arrangements the distance between ends 821 and 822 of opening 820 is about 0.1–0.3 inches, and most preferably about 0.19 inches. In the preferred arrangements, end 822 of opening 821 is located in the range of 0.05 to 0.75 inches from end 745 of trough member 700, most preferably in the range of about 0.06 to 0.4 inches. Also in the preferred embodiments, tab 780 has a length of 1 to 2 inches, most preferably a length of 1.25 to 1.5 inches.

For preferred arrangements, strap 730 is about 0.28 to 0.35 inches wide. Such a width will be comfortable for the wearer and convenient to use.

Figure 3:
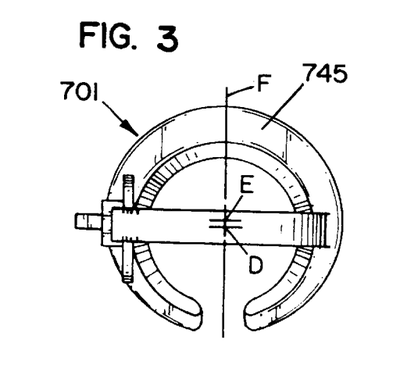
FIG. 3 is an opposite end elevational view of that shown in FIG. 2.

The outside diameter at end 745, FIG. 8, is molded to a diameter of 1.3–2.4 inches, preferably about 1.5–2 inches, most preferably about 1.75 inches. In the most preferred embodiment the inside diameter at end 745, FIG. 8 is concentric with the inside diameter at end 746, FIG. 8, as illustrated in FIG. 3 at D. However, in that most preferred embodiment, the outside diameter at end 745, FIG. 8 is offset from the inside diameter at end 745, FIG. 8 in the direction along line F, FIG. 3 toward point E, FIG. 3 a distance of about 0.15 to 0.25 inches, typically about 0.2 inches.

In addition to the advantages described above with respect to aiding sexual activity, the prosthesis also aids in maintaining a condom or similar device over the trough member 701, FIG. 6. In particular, when a condom or similar device is placed over trough member 701, the thickness of end 745, FIG. 3, aids in preventing the condom or similar device from slipping off during use. As described above, the retaining strap 730, FIG. 1 and retaining tab 708, FIG. 1, when placed around the wearer's scrotum and engaged as described above, aids in maintaining both the device 700 and the condom or similar device, in place over the user's penis during sexual activity. In the embodiment shown in FIG. 6, a condom is shown in phantom at reference 770. In the embodiment in FIG. 6, a shoulder 765 at end 745 is shown. The shoulder 765 will further aid the maintenance of the condom 770 over the trough member 701.

III. Detailed Description of the Embodiment of FIGS. 10–18

Since the filing date of Parent application Ser. No. 08/831, 605, further embodiments incorporating selected ones of the principles described in the parent disclosure. It will be understood that the arrangement of FIGS. 10–16 in many ways function generally analogously to the arrangements described in connection with FIGS. 1–9, and may be, except as described hereinbelow, constructed from similar materials and of similar dimensions. Certain specific improvements are provided, however, to advantage.

Figure 10:
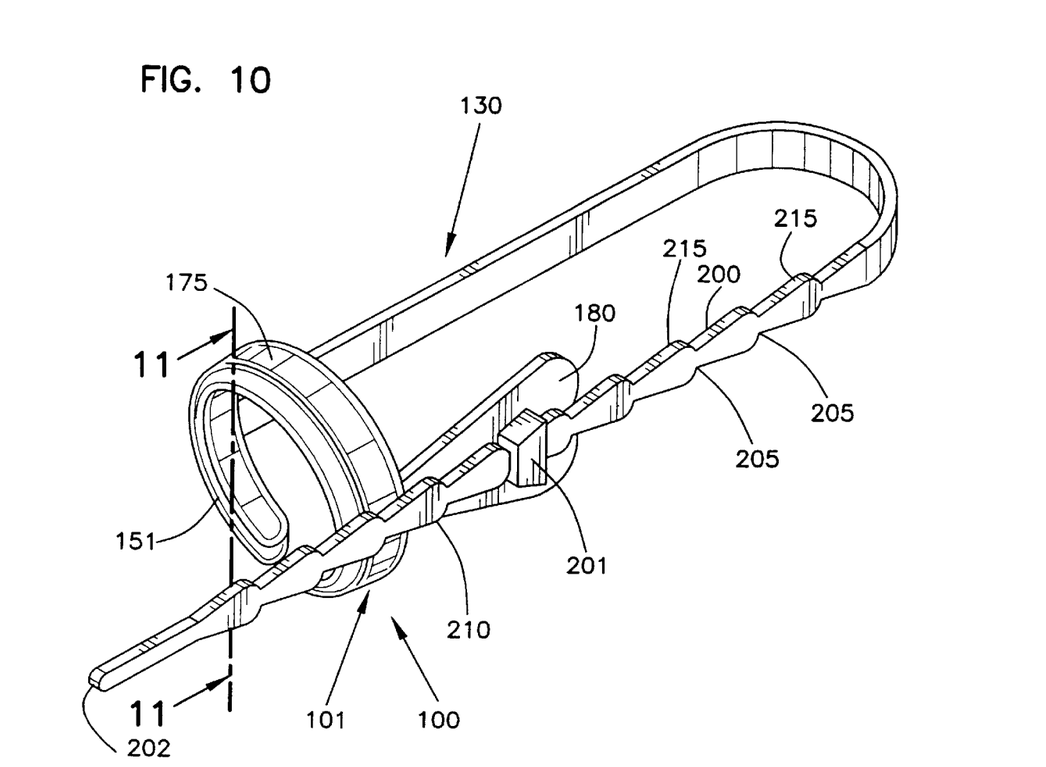
FIG. 10 is a perspective view of an alternate embodiment of a device according to the present invention.

Referring first to FIG. 10, the arrangement is shown generally at reference numeral 100. Preferably, the entire arrangement 100 is a molded construction comprising materials and methods of manufacture described above for the parent application.

The arrangement 100 generally includes one condom retention member 101; and, a mounting strap 130. The condom retention member is sized to fit over a penis of a user at a location immediately in front of the pubic bone. In some preferred embodiments, the condom retention member has a C-shaped cross section and longitudinal slot extending completely thereacross, similar to the device described in the parent application.

Figure 11:
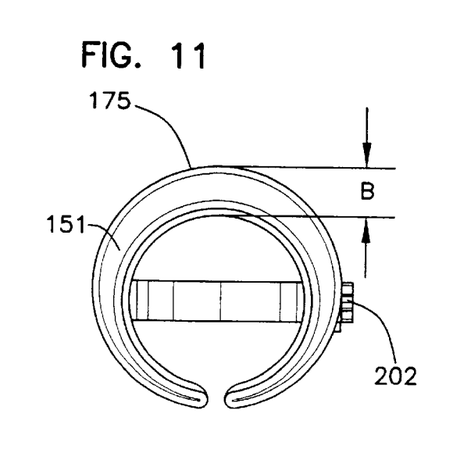
Figure 13:
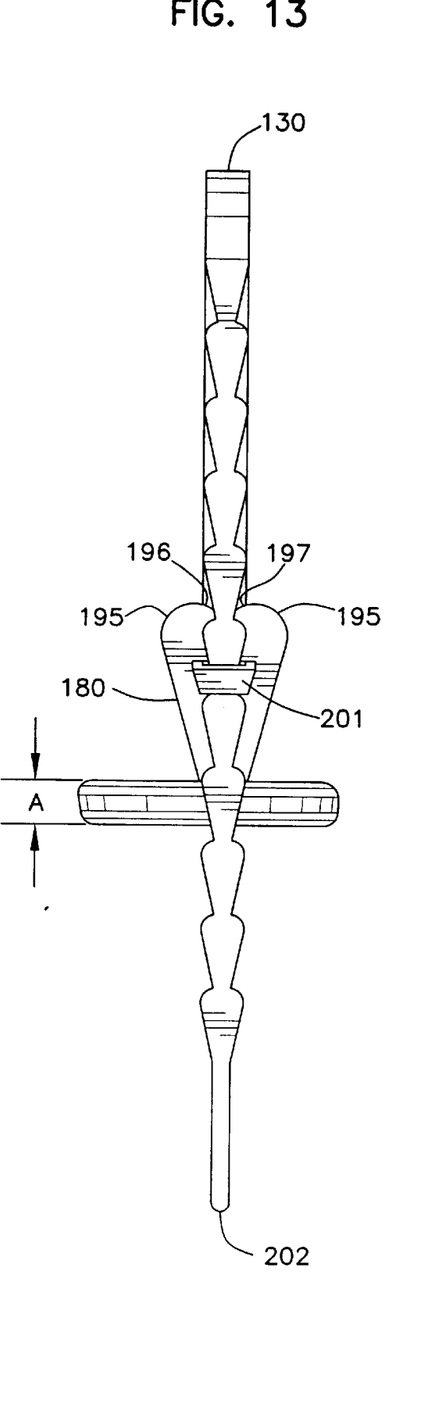
FIG. 13 is a side elevational view of the arrangement shown in FIG. 10.
Figure 14:
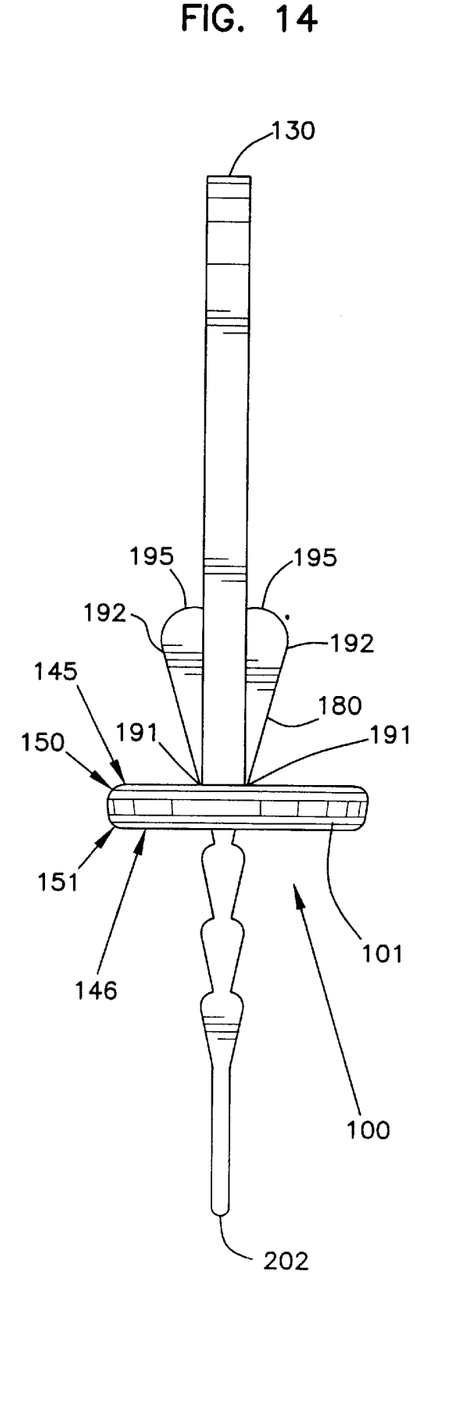
FIG. 14 is an opposite side elevational view to that shown in FIG. 13.

In addition to being molded from the Monsanto Santoprene® described above, preferably the condom retention member 101 of arrangement 100 has an overall length approximately equal to its thickness. Preferably the condom retention member 101 is as follows: its overall length, preferably as measured in projection as indicated in FIG. 13 at dimension A, is preferably no greater than 0.5 inches. (By "in projection" reference is meant to the length of the projected image, as shown, which may be slightly shorter than the actual length of the surface.) The thickness at dimension B, FIG. 11, is preferably similar to dimension B, FIG. 8. Preferably, the inside dimension at end 145, FIG. 14, is molded to a radius of curvature similar to end 745, FIG. 8. Preferably, the analogous inside radius of curvature at end 146, FIG. 14, is molded to a radius of curvature of about 0.01–0.1 inches smaller than the inside radius of curvature of end 145. In use, the arc made by the preferred embodiment of the condom retention member 101 will consist of an arc of between about 200 to 340 degrees, and most preferably between about 240 to 300 degrees.

The radii of curvature at certain portions of the arrangement have been designed for preferred levels of comfort. The radius of curvature at edge 150, FIG. 14, (the outer edge of end 145) is preferably molded similarly to edge 750, FIG. 8. The radius of curvature at edge 151, FIG. 14, (the outer edge of end 146) is preferably molded similarly to edge 150.

Figure 16:
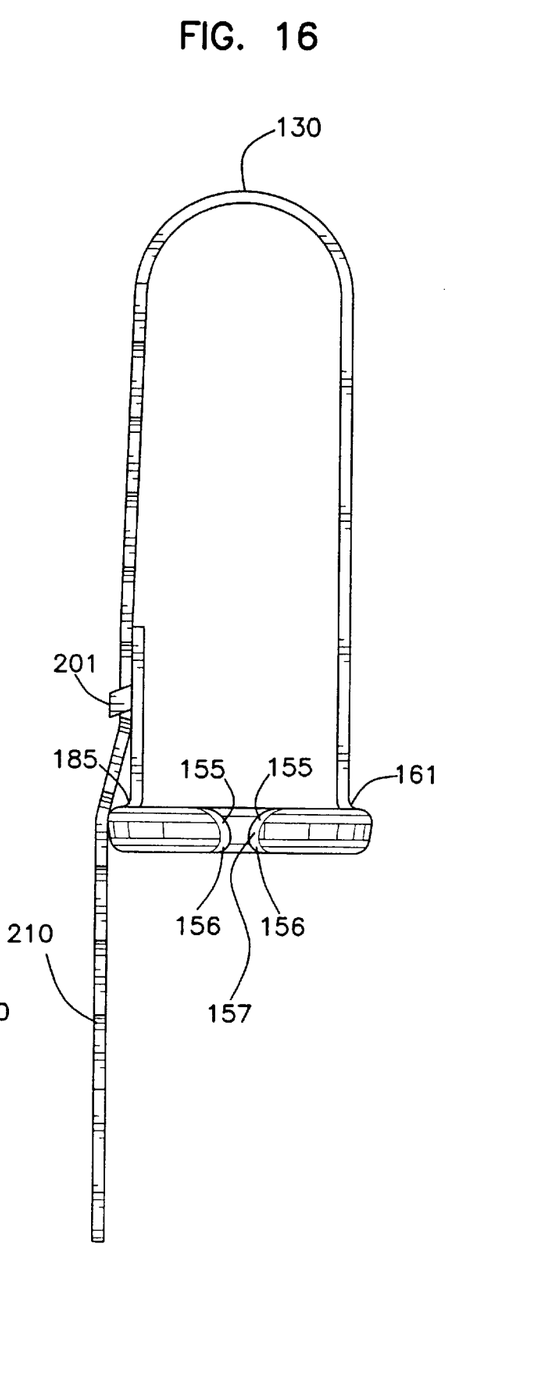
FIG. 16 is a bottom plan view of the arrangement shown in FIG. 10.

Referring to FIG. 16, preferably the radius of curvature for edges or corners 155 is similar to edges 755, FIG. 7. Slot 157, FIG. 16 may be as described above for U.S. Pat. No. 5,360,390, with a similar width and definition by arcuate extension.

At corners 156, FIG. 16, preferably the radius of curvature is similar to corners 155.

It has been found that when molded to the general dimensions described hereinabove, arrangements 100 according to the present invention will be shaped in a convenient, comfortable, manner that is effective for facilitating use, on the average wearer.

Attention is now directed to features which concern the mounting strap 130, FIG. 10, and the manner in which it is mounted in the arrangement 100. Reference numerals 200, 202, 205, 210, and 215 are analogous to reference numerals 100, 802, 805, 810, and 815, in FIG. 1, respectively. In addition, with respect to the mounting strap 130, FIG. 15, reference numerals 160, 161, 165, and 166 are analogous to reference numerals 730, 760, 761, 765, and 766, in FIG. 6, respectively.

Figure 15:
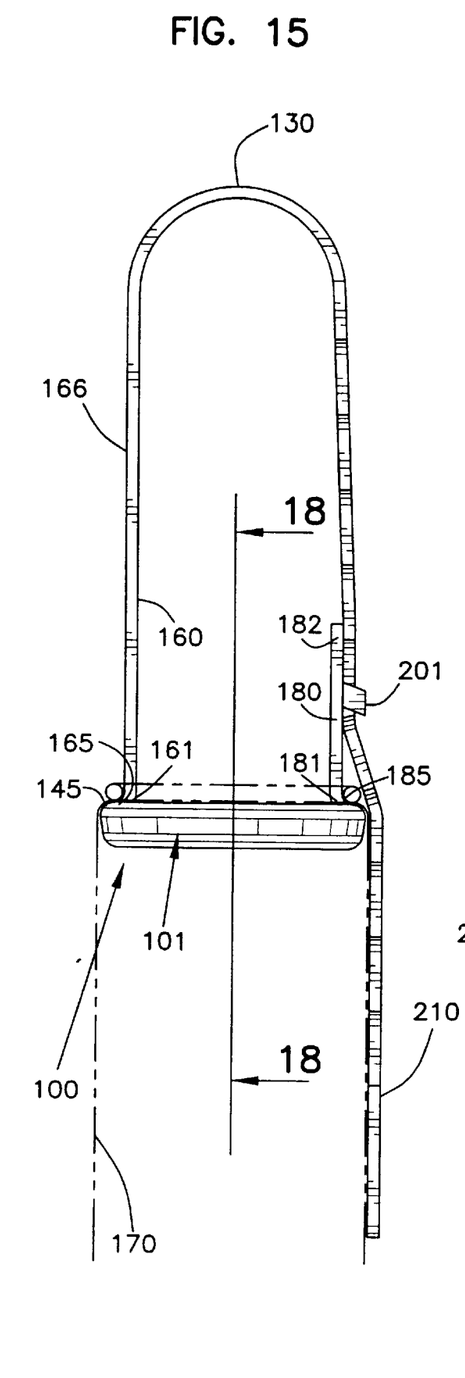
FIG. 15 is a top plan view of the arrangement shown in FIG. 10.

Attention is now directed to features which concern the receiving tab 180, FIG. 15. Reference numerals 180, 181, 182, 185, and 201 are analogous to reference numerals 780, 781, 782, 785, and 801, in FIG. 6, respectively. Reference numerals 191, 192, and 195, in FIG. 14, are analogous to reference numerals 791, 792, and 795, in FIG. 5, respectively. Reference numerals 196, and 197, in FIG. 13, are analogous to reference numerals 796, and 797, in FIG. 5, respectively.

Referring to FIG. 15, strap 130 is preferably molded such that an inside surface 160 of strap 130 is approximately flush with (or coplanar with) an inside surface of portion 101, similar to the preferred embodiment of inside surface 760, FIG. 6. By constructing the overall molded arrangement 100 such that an inside surface 160 of strap 130 is approximately flush with (or coplanar with) an inside surface of portion 101, instead of having the inside surface 160 or an outside surface 166 of strap 130 approximately flush with (or coplanar with) end 145 of condom retention member 101, the strap 130 is much less likely to break away from the end 145 of condom retention member 101, in use. Also preferably strap 130, at point 161, FIG. 15, whereat it is attached to condom retention member 101, has a thickness similar to strap 730, FIG. 6. In the preferred embodiments, preferably an outer lip or shoulder at 165 where strap 130 attaches to condom retention member 101 is left. This lip or shoulder 165 provides a recess into which an open end of a condom or lubricated cover, shown in phantom in FIG. 15 at reference numeral 170, can be positioned (rolled) in use. This shoulder 165 will tend to maintain the condom or lubricated cover securely on the user and arrangement 100, during use, to advantage. In some preferred embodiments this is facilitated by the absence of a bead along outer surface 175, of condom retention member 101, FIG. 10. That is, in some preferred embodiments outer surface 175 generally is flat or planar, with the curved ends as described, and it does not have an upwardly or outwardly raised bead or projection thereon, at any location, and the outer surface 175 has rounded ends 151 and 150 as described. In other preferred embodiments, outer surface 175 may have a series of raised ribs along its length, or a series of bumps or other surface configurations.

Referring to FIG. 15, preferably the arrangement 100 includes a receiving tab 180 molded to condom retention member 101 at a location 181 generally opposite of location 161 whereat strap 130 attaches. Preferably, member 180 has a thickness generally the same as that of the strap 130. Also preferably, member 180 is analogously molded with an inside surface 182 approximately flush or coplanar with an inside surface of condom replacement member 101. Further, preferably it is molded such that shoulder 185, analogous to shoulder 165, is provided, for analogous reasons.

The particular "heart shaped" outer configuration for member 180 illustrated in FIGS. 13 and 14, by periphery 195, provides no distinct advantage, and is present as an artistic feature for aesthetic purposes. Also, in part, it was designed to serve a distinctive source identifying function, i.e. that the arrangement originated with the present assignee. It will be readily understood that advantageous narrow portions at area 191, and a wide portion somewhere else in member 180 could be accomplished with many variations in outer periphery. The two rounded lobes at 196 and 197, provide a somewhat "heart-shaped" design, and do not specifically serve advantage.

Again, there are, however, advantages similar to the advantages described for points 792, FIG. 5, to having a relatively wide portion as indicated between points 192.

Figure 17:
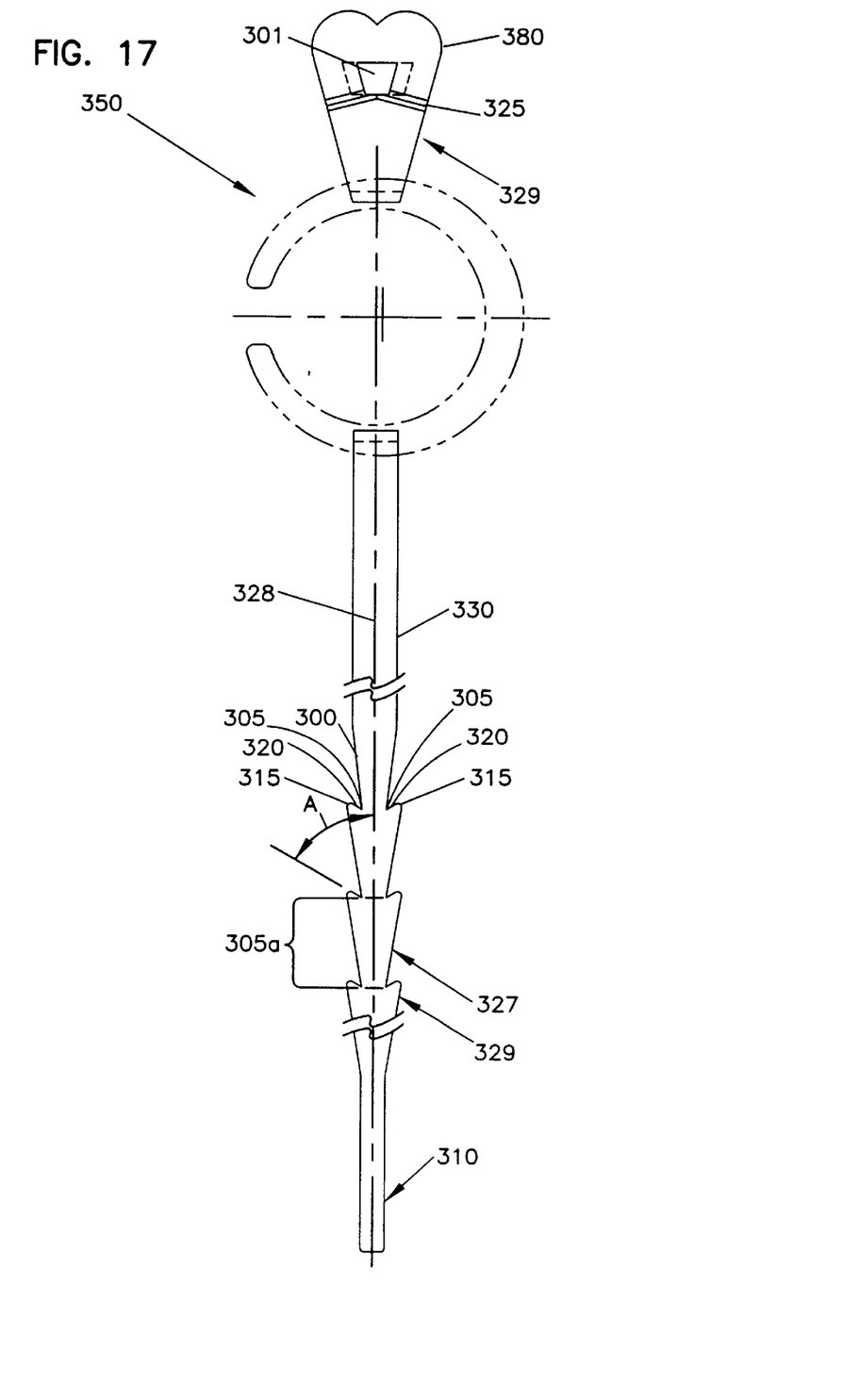
Figure 18:
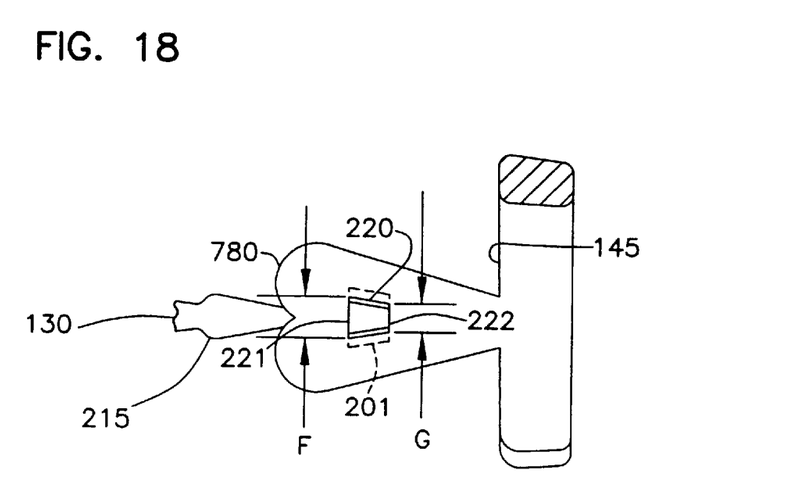
FIG. 18 is a fragmentary cross-sectional view of the arrangement shown in FIG. 10, taken generally along line 18—18, FIG. 15.

When single use is desired, it may be preferred to have a device 100 which does not allow for easy retraction of strap 130, FIGS. 10 and 15, without breaking the device 100. In FIG. 17, an example of a modified device 350, that is generally analogous in detail to the device 100 described in FIGS. 10–23, except as described hereinbelow, is depicted. In the preferred embodiment depicted in FIG. 17, reference numerals 300, 301, 305, 305a, 310, 315, 320, 327, 328, 329, 330, 350, and 380 are analogous to reference numerals 900, 901, 905, 905a, 910, 915, 920, 927, 928, 929, 930, 950, and 980, in FIG. 9, respectively. Angle A in FIG. 17 is analogous to angle A in FIG. 9.

Figure 12:
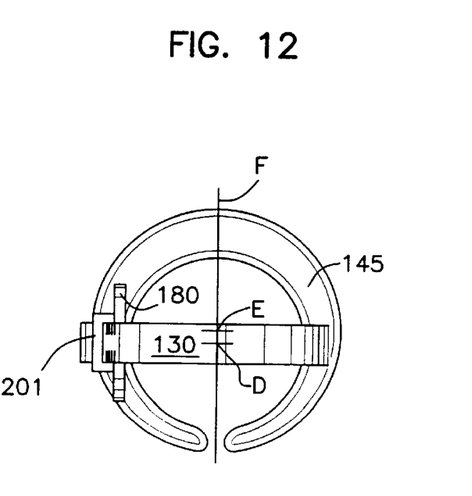
FIG. 12 is an opposite end elevational view to that shown in FIG. 11.

The outside diameter at end 145, FIG. 12, is preferably molded to a diameter of 1.3–2.4 inches, more preferably about 1.5–2 inches, most preferably about 1.75 inches. In the most preferred embodiment the inside diameter at end 145, FIG. 23 is concentric with the inside diameter at end 146, FIG. 23, as illustrated in FIG. 12 at D. However, in the most preferred embodiment, the outside diameter at end 145, FIG. 12 is offset from the inside diameter at end 145, FIG. 23 in the direction along line F, FIG. 12 toward point E, FIG. 12 a distance of about 0.15 to 0.25 inches, typically about 0.2 inches.

What is claimed and desired to be secured by letters patent is as follows:

1. A combination for retaining a condom on a human male; said combination comprising:
 (A) a condom having a first end being closed and a second end being open;
 (B) a retention device for use by a human male; said device comprising:
  (i) a member sized to fit on a penis of a user;
   (a) said member having an outer surface with first and second ends;

(b) said member having a shoulder on said second end;
(ii) a retaining construction for maintaining the member in operative association on the user's penis, during performance of intercourse; said retaining construction comprising: a retaining strap having first and second ends; and, a retaining tab;
  (a) said retaining strap and retaining tab each being secured to said member second end;
  (b) said retaining strap being constructed and arranged for selective locking engagement with said retaining tab, in use;
  (c) each of said retaining strap and said retaining tab is thinner than said second end of said member; and,
(C) said condom being positioned on said member, with the second end of said condom positioned over said shoulder.

2. A combination according to claim 1 wherein:
(A) said retaining tab has a first end whereat it is attached to said member; said first end of said retaining tab having a first dimension of width; and,
(B) said retaining tab is configured to have a second dimension of width, at a portion thereof spaced from said member, said second dimension of width being greater than said first dimension of width.

3. A combination according to claim 2 wherein:
(A) said second dimension of width is at least 0.75 times larger than said first dimension of width.

4. A combination according to claim 2 wherein:
(A) said first dimension of width is within the range of 0.25 to 0.5 inches; and,
(b) said second dimension of width is within the range of 0.5 to 1 inches.

5. A retention device for use by a human male; said device comprising:
(A) a member sized to fit on a penis of a user;
  (i) said member having an outer surface and an inner surface with first and second ends;
  (ii) said member being constructed and arranged with the greatest dimension between said outer surface and said inner surface being approximately the same as the greatest dimension between said first and said second ends;
(B) a retaining construction for maintaining the member in operative association on the user's penis, during performance of intercourse; said retaining construction comprising: a retaining strap having first and second ends; and, a retaining tab;
  (i) said retaining strap and retaining tab each being secured to said member second end;
  (ii) said retaining strap being constructed and arranged for selective locking engagement with said retaining tab, in use;
  (C) each of said retaining strap and said retaining tab are thinner than said second end of said member; and,
    (i) said retaining strap and retaining tab each being secured to said member with a shoulder formed along said member second end, between each of said retaining strap and retaining tab, and an outer surface of said member and with said condom covering said member outer surface with said condom second end mounted in said shoulder.

6. A retention device according to claim 5 wherein the greatest distance between said first and second ends is no greater than 0.5 inches.

7. A retention device according to claim 6 wherein:
(A) said member has a C-shaped cross-section.

8. A retention device according to claim 6 wherein:
(A) said member is a ring.

9. A retention device according to claim 6 wherein:
(A) said member is a molded construction comprising flexible urethane.

10. A retention device according to claim 6 wherein:
(A) said member is a molded construction comprising latex.

11. A retention device according to claim 6 wherein:
(A) said retention device comprises a unitary, molded, construction without any attachment seams.

12. A method of preparing a human male for sexual activity; said method comprising the steps of:
(A) fitting over a user's penis a retention device comprising:
  (i) a member sized to fit on a penis of a user;
    (a) having an outer surface with first and second ends;
    (b) having a shoulder on said second end;
  (ii) retaining means for maintaining the member in operative association on the user's penis, during performance of intercourse; said retaining means comprising: a retaining strap having first and second ends; and, a retaining tab; said retaining strap and retaining tab each being secured to said member second end; said retaining strap having structure thereon for selective locking engagement with said retaining tab, in use; and,
  (iii) each of said retaining strap and said retaining tab being thinner than said second end of said member;
(B) said step of fitting the user's penis with the retention device including:
  (i) positioning the retention device on the penis;
  (ii) positioning the retaining strap around the user's scrotum; and,
  (iii) engaging the retraining strap with the retaining tab,
(C) fitting over a user's penis and said member of said retention device a condom.

\* \* \* \* \*